(12) United States Patent
Lobbins et al.

(10) Patent No.: US 8,303,569 B2
(45) Date of Patent: *Nov. 6, 2012

(54) COMPOSITE LAMINATED CATHETER WITH FLEXIBLE SEGMENT AND METHOD OF MAKING SAME

(75) Inventors: Jonathon M. Lobbins, Burlington, MA (US); Kenneth D. Warnock, Jr., Manchester-by-the-Sea, MA (US); Michelle Provost, North Andover, MA (US); Lee Core, Cambridge, MA (US); Michael Papa, Beverly, MA (US); Michael Riopel, Ipswich, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 962 days.

This patent is subject to a terminal disclaimer.

(21) Appl. No.: 11/562,042

(22) Filed: Nov. 21, 2006

(65) Prior Publication Data

US 2007/0250039 A1    Oct. 25, 2007

(51) Int. Cl.
*A61M 25/00* (2006.01)
*B29C 65/00* (2006.01)

(52) U.S. Cl. .................................. 604/525; 156/229

(58) Field of Classification Search .............. 604/95.01, 604/264, 523–528; 128/656–658; 156/159, 156/229, 167
See application file for complete search history.

(56) References Cited

U.S. PATENT DOCUMENTS

| | | | |
|---|---|---|---|
| 5,011,469 A * | 4/1991 | Buckberg et al. | 604/6.11 |
| 5,037,404 A * | 8/1991 | Gold et al. | 604/527 |
| 5,061,257 A * | 10/1991 | Martinez et al. | 604/526 |
| 5,267,958 A * | 12/1993 | Buchbinder et al. | 604/103.14 |
| 5,308,342 A * | 5/1994 | Sepetka et al. | 604/525 |
| 5,676,659 A * | 10/1997 | McGurk | 604/527 |
| 5,702,373 A * | 12/1997 | Samson | 604/527 |
| 5,711,909 A * | 1/1998 | Gore et al. | 264/320 |
| 5,755,704 A | 5/1998 | Lunn | |
| 5,772,642 A | 6/1998 | Ciamacco, Jr. et al. | |
| 5,817,071 A | 10/1998 | Dewindt et al. | |
| 5,851,203 A * | 12/1998 | van Muiden | 604/525 |
| 6,059,769 A * | 5/2000 | Lunn et al. | 604/523 |
| 6,368,316 B1 * | 4/2002 | Jansen et al. | 604/526 |
| 6,375,774 B1 * | 4/2002 | Lunn et al. | 156/158 |
| 6,824,553 B1 * | 11/2004 | Samson et al. | 606/192 |
| 6,931,899 B2 | 8/2005 | Goff et al. | |
| 6,945,956 B2 * | 9/2005 | Waldhauser et al. | 604/95.01 |
| 7,010,953 B2 | 3/2006 | Stupecky | |
| 7,037,295 B2 | 5/2006 | Tiernan et al. | |
| 7,276,043 B2 * | 10/2007 | Heath et al. | 604/6.16 |
| 2002/0156459 A1 * | 10/2002 | Ye et al. | 604/527 |
| 2002/0156460 A1 * | 10/2002 | Ye et al. | 604/534 |
| 2004/0015151 A1 * | 1/2004 | Chambers | 604/532 |
| 2004/0225278 A1 * | 11/2004 | Poole et al. | 604/523 |
| 2005/0004594 A1 | 1/2005 | Nool et al. | |

FOREIGN PATENT DOCUMENTS

JP    7096036 A1    4/1995

* cited by examiner

*Primary Examiner* — Kevin C Sirmons
*Assistant Examiner* — William Carpenter (57) ABSTRACT

A medical catheter including a composite laminated shaft having a longitudinal segment that is mechanically deformed to have reduced and varying stiffness. A method of making the catheter is also disclosed.

11 Claims, 7 Drawing Sheets

COMPOSITE LAMINATED CATHETER WITH FLEXIBLE SEGMENT AND METHOD OF MAKING SAME

FIELD OF THE INVENTION

The present disclosure relates generally to a medical catheter having variable flexibility along its length, and more particularly, to a composite laminated catheter with a mechanically deformed segment having reduced stiffness.

BACKGROUND OF THE INVENTION

A stenosis, or narrowing of a blood vessel such as an artery may comprise a hard, calcified substance and/or a softer thrombus (clot) material. There have been numerous therapeutic procedures developed for the treatment of stenosis in an artery. One of the better-known procedures is percutaneous transluminal coronary angioplasty (PTCA). According to this procedure, the narrowing in the coronary artery can be reduced by positioning a dilatation balloon across the stenosis and inflating the balloon to re-establish acceptable blood flow through the artery. Additional therapeutic procedures may include stent deployment, atherectomy, and thrombectomy, which are well known and have proven effective in the treatment of such stenotic lesions. Distal occlusion or filtration, with or without aspiration embolectomy, have also been developed as adjunctive procedures to prevent downstream embolization by collecting and removing atheroembolic debris that may be generated during any of the above therapies. Increasingly specialized aspiration catheters have been developed for aspiration of body fluids contaminated with thrombus or embolic debris before, during and/or after an arterial intervention.

The therapeutic procedure typically starts with the introduction of a guiding catheter into the cardiovascular system from a convenient vascular access location, such as through the femoral artery in the groin area or other locations in the arm or neck. The guiding catheter is advanced through the arteries until its distal end is subselectively located in a branch vessel leading to the stenosis that is targeted for treatment. During PTCA, for example, the distal end of the guiding catheter is typically inserted only into the origin of a native or bypass graft coronary artery. A guidewire is advanced through a central bore in the guiding catheter and positioned across the stenosis. An interventional therapy device, such as a balloon dilatation catheter, is then slid over the guidewire until the dilatation balloon is properly positioned across the stenosis. The balloon is inflated to dilate the artery. To help prevent the artery from re-closing, a physician can implant a stent inside the artery. The stent is usually delivered to the artery in a compressed shape on a stent delivery catheter and expanded by a balloon for implantation against the dilated arterial wall. Prior to the insertion and use of the interventional therapy catheter, an aspiration catheter may be advanced over the guidewire and used to suction thrombus that may be clinging to the stenosis. An aspiration catheter can also be used following the therapy catheter to remove contaminated blood that has been held close to the treatment area by temporary occlusion or filtration devices.

In order for the physician to direct the guiding catheter and/or aspiration catheter to the correct location in the vessel, the physician must apply longitudinal forces, and sometimes apply rotational forces. For the catheter to transmit these forces from the proximal end to the distal end, the catheter must be rigid enough to be pushed through the blood vessel, a property sometimes called pushability, but yet flexible enough to navigate the bends in the blood vessel. The catheter may also require sufficient torsional stiffness to transmit the applied torque, a property sometimes called torqueability. To accomplish this balance between longitudinal rigidity, torsional stiffness, and flexibility, there is often a support member added to the catheter shaft. This support member is often comprised of a woven reinforcement or coiled filament embedded in the shaft. This support wire is often embedded between two adherent layers of tubing to form a composite laminated catheter shaft.

Using the femoral artery approach in a PTCA procedure, a catheter is passed upward through the aorta, over the aortic arch, and down to the coronary artery to be treated. It is preferable the guiding catheter or aspiration catheter have a soft tip or flexible section for atraumatically passing through the selected vessels. Therefore, it is advantageous to have the proximal section be rigid to transmit the applied forces, but to have a distal section be more flexible to allow for better placement of the catheter distal section within tortuous vasculature. The need for this combination of performance features makes it desirable for a catheter shaft to have variable flexibility along the length of the catheter. More specifically, it is desirable for a catheter to have increased flexibility near the distal end of the catheter shaft and greater stiffness near the proximal end.

One approach used to balance the need for pushability and torqueability while maintaining adequate flexibility has been to manufacture a catheter that has two or more discrete tubular portions over its length, each having different performance characteristics. For example, a relatively flexible distal section may be connected to a relatively rigid proximal section. When a catheter is formed from two or more discrete tubular members, it is often necessary to form a bond between the distal end of one tubular member and the proximal end of another tubular member. This method requires substantial manufacturing steps to assemble the various sections and makes it difficult to manufacture the entire catheter shaft utilizing low-cost coextrusion technology. Further, such a shaft design may include relatively abrupt changes in flexibility at locations where material changes occur. Besides being cumbersome to manufacture, a catheter with abrupt changes in flexibility may be susceptible to kinking at such stress concentrations.

Various other approaches for achieving variable stiffness of the catheter shaft include varying the braid pitch of the reinforcement layer and/or varying the properties of materials used in construction, such as by removing a selected distal portion of an outer tubular layer of the catheter shaft and replacing that distal portion with one or more sections of more flexible tubing. A unitary catheter shaft arrangement with variable stiffness is also known that incorporates one or more layers of a material that is curable by ultraviolet light, wherein selected portions of the catheter shaft are subjected to radiation to cure, the material and thereby increase the stiffness of the shaft in the treated area. Another catheter having variable stiffness is taught in U.S. Patent Application Publication No. U.S. 2004/0225278 A1 to Poole, et al. The Poole, et al. publication teaches a catheter having varying stiffness achieved by making lamination bonds of varying integrity between a liner and an outer shell.

However, a need still exists for guiding catheter shafts that can be easily manufactured, such as by continuous extrusion, co-extrusion and/or other reel-to-reel processes, and have a variable stiffness without assembling multiple components of the shaft or attending to difficulties inherent in irradiated variable-stiffness catheters, such as the limitations in the choice of catheter materials and in the control of the final catheter properties.

SUMMARY OF THE INVENTION

An embodiment of the present disclosure is a catheter for placement in a patient's vessels, such as the vasculature. The catheter includes a composite laminated catheter shaft comprising an elongate flexible liner, an elongate flexible jacket surrounding the liner, and a reinforcement layer interposed between the liner and the jacket. A segment of the shaft is mechanically deformed to have reduced stiffness. The disclosure is applicable to various kinds of composite laminated catheters, including guiding catheters having a curvilinear portion and aspiration catheters having a dual lumen portion.

Another embodiment of the present disclosure is a method of making a composite laminated catheter shaft comprising an elongate flexible liner having, an elongate flexible jacket surrounding the liner, and a reinforcement layer interposed between the liner and the jacket. A segment of the shaft is mechanically deformed to have reduced stiffness.

BRIEF DESCRIPTION OF THE DRAWINGS

The novel features of this disclosure, as well as the disclosure itself, both as to its structure and its operation, will be best understood from the accompanying drawings, taken in conjunction with the accompanying description, in which similar reference characters refer to similar parts, and in which.

DETAILED DESCRIPTION OF THE INVENTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician "Proximal" and "proximally" are a position near or in a direction toward the clinician.

The following detailed description is merely exemplary in nature and is not intended to limit the disclosure or the application and uses of the disclosure. Although the description of the disclosure is in the context of guiding catheters and aspiration catheters for treatment of coronary arteries, the disclosure is not so limited, and the disclosure may be useful for other types of catheters and for treatment of other blood vessels such as carotid, renal or any other peripheral, viz. non-coronary arteries. A catheter embodying one or more features of the disclosure may or may not have a lumen or bore there through, and the catheter may also carry therapeutic or sensing elements, e.g., balloons, electrodes or stents, and may be used in other body passageways where it is deemed useful. Furthermore, there is no intention to be bound by any expressed or implied theory presented in the preceding technical field, background, brief summary or the following detailed description.

Figure 1:
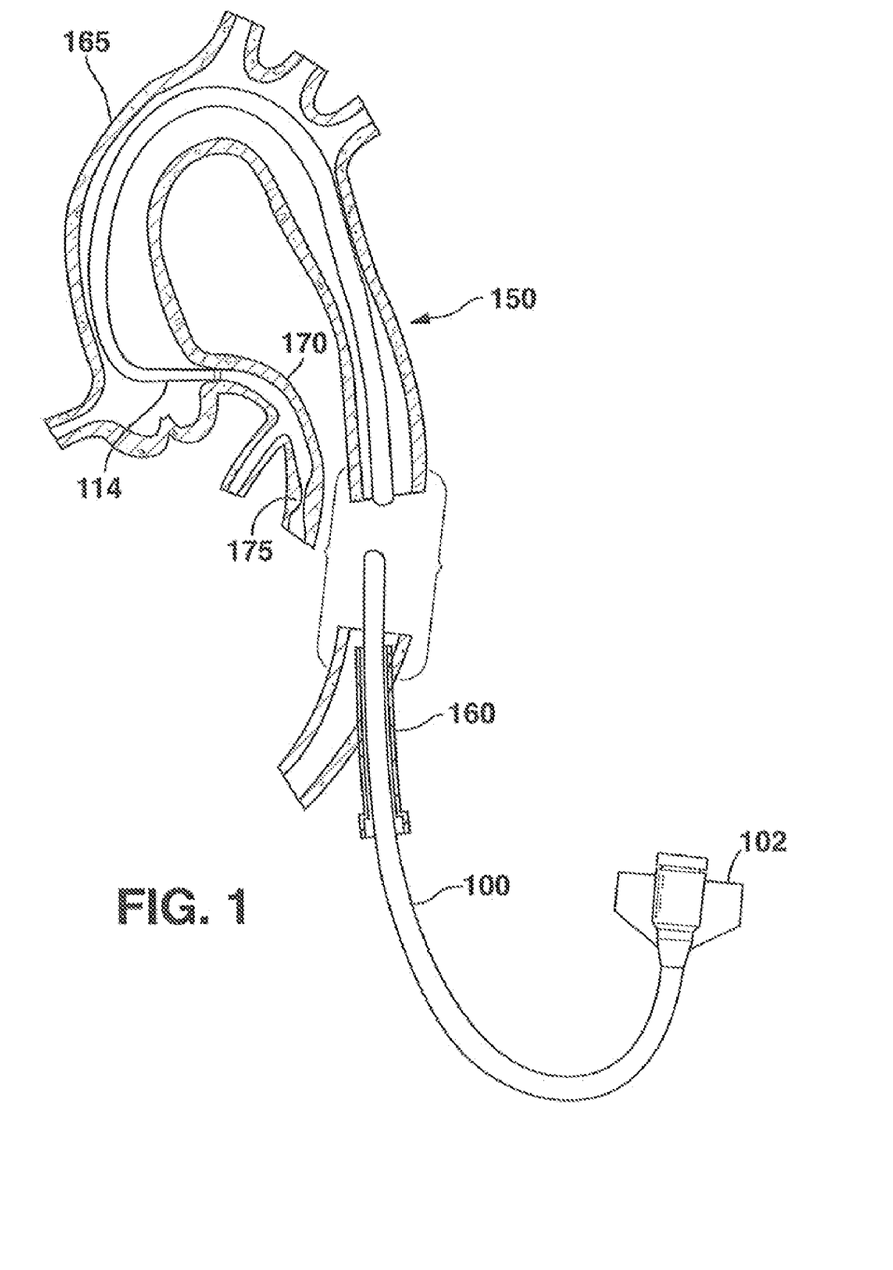
FIG. 1 illustrates a gliding catheter according to an embodiment of the present disclosure shown positioned within a patient's vascular system.

FIG. 1 illustrates guiding catheter 100 for use with a therapeutic device (not shown) positioned within a patient's vascular system 150. In a representative use of the catheter, the clinician inserts a distal end of guiding catheter 100 through introducer sheath 160 into vascular system 150, typically through a femoral artery in the groin area. Guiding catheter 100 is then advanced through aorta 165 until the distal end of the catheter is located in the ostium of a targeted branch artery 170. In the example shown branch artery 170 is a patient's left coronary artery, and the distal end of guiding catheter 100 is positioned proximal of a stenosis 175. Once positioned, a therapeutic device, such as a balloon dilatation catheter including a dilatation balloon, may be advanced through guiding catheter 100 to provide treatment of stenosis 175. Upon completion of the interventional procedure and removal of any therapeutic device, guiding catheter 100 is withdrawn from the patient's vascular system 150.

Figure 2:
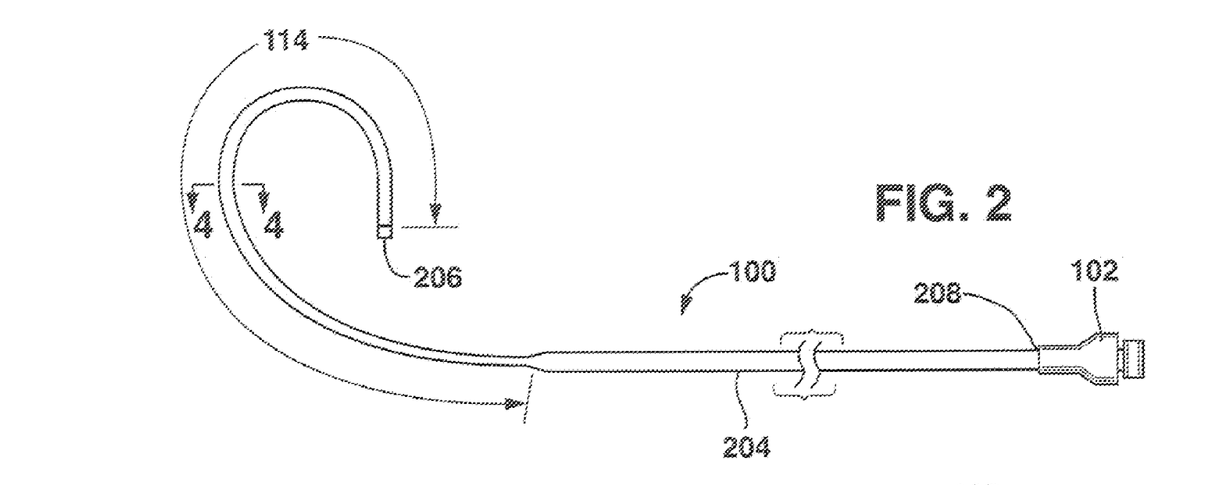
FIG. 2 illustrates a side view of the guiding catheter of FIG. 1.
Figure 4:
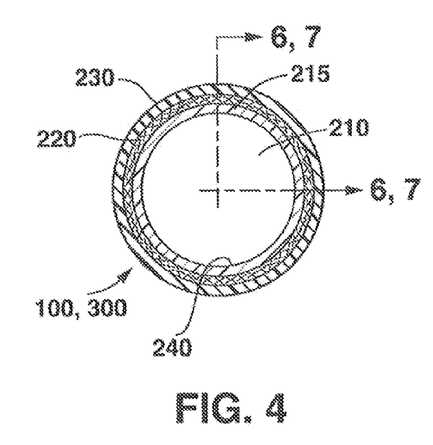
FIG. 4 is a transverse cross-sectional view of the catheters of FIGS. 2 and 3 taken along lines 4-4.

FIG. 2 illustrates a side view of an embodiment of guiding catheter 100, including, in elongate shaft 204 with a distal end 206 having an optional soft tip. As shown in FIG. 4, a bore or lumen 210 extends through shaft 204 between an open proximal end 208 and distal end 206. In an embodiment of the present disclosure, bore 210 has a low-fiction surface and is sized and shaped to receive and direct there through a variety of treatment devices, such as guidewires and/or therapeutic devices including, but not limited to balloon catheters, stent delivery systems, or aspiration catheters. In another embodiment, bore surface 240 may provide a slippery interior surface for reducing frictional forces between the interior surface of guiding catheter 100 and devices that may be moved through bore 210.

A connector fitting 102 is coupled to, and provides a functional access port at proximal end 208 of guiding catheter 100. Fitting 102 is attached to catheter shaft 204 and has a central opening in communication with open proximal end 208 and bore 210 to allow passage of various fluids and/or therapeutic devices there through. Connector fitting 102 may be made of metal or of a hard polymer, e.g. medical grade polycarbonate, polyvinyl chloride, acrylic, acrylonitrile butadiene styrene (ABS), or polyamide, that possesses the requisite structural integrity, as is well known to those of ordinary skill in the art.

Catheter shaft 204 is a single lumen tubular structure that is designed to advance through a patient's vasculature to remote arterial locations without buckling or undesirable bending. In an embodiment of the present disclosure, catheter shaft 204 also has reduced stiffness within at least flexible segment 114. Catheter shaft 204 may include a preformed curvilinear shape in a distal portion for providing backup support as therapeutic catheters are advanced through bore 210 of guiding catheter 100 and across stenosis 175. As shown in FIG. 2, any one of a number of pre-formed curvilinear shapes may be incorporated into guiding catheter 100, such as Judkins-type or Amplatz-type curves, as non-limiting examples.

Figure 3:
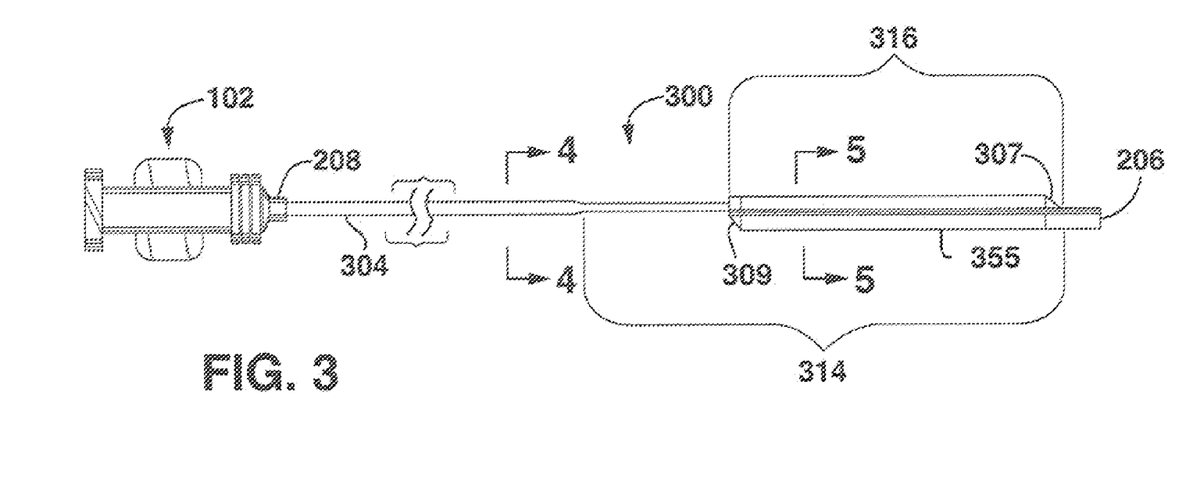
FIG. 3 illustrates a side view of an aspiration catheter according to an embodiment of the present disclosure.

FIG. 3 illustrates a side view of an embodiment of an aspiration catheter 300, which has several inventive features in common with guiding catheter 100. Aspiration catheter 300 includes an elongate shaft 304 with a distal end 206 having an optional soft tip. As shown in FIG. 4, bore 210 extends through shaft 304 between open proximal end 208 and distal end 206. Connector fitting 102 is coupled to, and provides a functional access port at proximal end 208 of aspiration catheter 300. Fitting 102 is attached to catheter shaft 304 and has a central opening in communication with open proximal end 208 and bore 210 to allow passage of various body fluids there through. In an embodiment of the present disclosure, catheter shaft 304 also has reduced stiffness within at least flexible segment 314.

Figure 5:
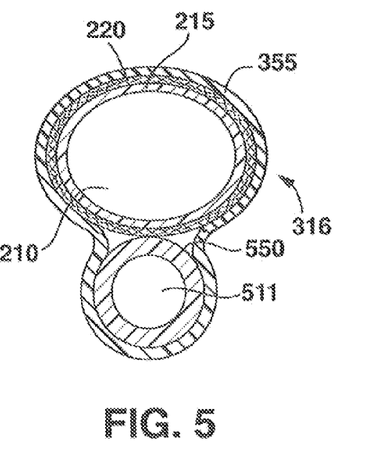
FIG. 5 is a transverse cross-sectional view of the aspiration catheter of FIG. 3 taken along line 5-5.

Single operator aspiration catheter 300 includes a dual lumen portion 316 that is substantially shorter than the full length of catheter 300. In the embodiment shown in FIG. 3, dual lumen portion 316 is shorter than flexible segment 314 and comprises a distal portion of segment 314. Other arrangements are also possible, including, but not limited to dual lumen portion 316 comprising a middle portion, a proximal portion, or all of flexible segment 314. Dual lumen portion 316 extends proximally from distal fluid port 307 disposed at or adjacent the distal end of tubular body 304 to open proximal end 309 of guidewire lumen 511. As shown in transverse cross-section at FIG. 5, dual lumen portion 316 comprises guidewire tube 550 extending alongside flexible segment 314 of catheter shaft 304 to arrange aspiration lumen 210 and guidewire lumen 511 in a parallel or side-by-side configuration. At least within dual lumen portion 316, jacket 230 is absent from catheter shaft 304; jacket 230 having been selectively removed from at least a portion of shaft 304. Within dual lumen portion 316, over sleeve 355 surrounds and secures together guidewire tube 550 and flexible segment 314 of shaft 304. A process for selectively removing a portion of jacket 230, and for positioning and attaching guidewire tube 550 and over sleeve 355 to make dual lumen portion 316 will be discussed further below with regard to FIG. 12.

FIG. 4 illustrates a transverse cross-section of composite laminated catheters 100 and 300, as the cross sections would appear in shafts 204, 304 and in flexible segments 114, 314. As shown in FIG. 4, catheter shafts 204, 304 include a liner 215, a reinforcement layer 220, and a jacket 230. Liner 215 is tubular and defines bore 210, which is sized and shaped as described above. In a guiding catheter embodiment of the present disclosure, those of ordinary skill in the art may appreciate that any one of numerous low-friction, biocompatible materials such as, for example, fluoropolymers (e.g. PTFE, FEP), polyolefins (e.g. polypropylene, high-density polyethylene), or high density polyamides, may be used to make liner 215 or to make a coating on surface 240 of bore 210 to provide good flexibility and good movement of catheter 100 over a guidewire and/or good movement of a therapeutic device within guiding catheter 100. In an embodiment such as aspiration catheter 300, where aspirating fluids through bore 210 is not facilitated by having a low coefficient of friction on surface 240, liner 215 may comprise alternative materials such as a relatively lower-density polyamide or a polyethylene block amide copolymer (PEBA). In the present embodiment of aspiration catheter 300, liner 215 comprises PEBA 70D, viz. having a hardness or durometer of 70 on the shore D scale.

Reinforcement layer 220 enhances the torsional strength and inhibits kinking of catheter shaft 204, 304 during advancement of catheters 100, 300 within the patient's vasculature. Reinforcement layer 220 is positioned between and is substantially coaxial with liner 215 and jacket 230. In various embodiments, reinforcement layer 220 may be formed by braiding multiple filaments or winding at least one filament over liner 215 or by applying a metal mesh over inner layer 215. Braided or wound filaments may comprise high-modulus thermoplastic or thermo-set plastic materials, e.g., liquid crystal polymer (LCP), polyester, or aramid polymer e.g. poly-paraphenylene terephthalamide (Kevlar® from E.I. du Pont de Nemours and Company, Wilmington, Del., U.S.A.). Alternatively, braided or wound filaments may comprise metal wires of stainless steel, superelastic alloys such as nitinol (TiNi), refractory metals such as tantalum, or a work-hardenable super alloy comprising nickel, cobalt, chromium and molybdenum. The reinforcing filaments may have cross sections that are round or rectangular, i.e. flat or ribbon shapes.

Examples of woven or braided reinforcement layer 220 may include one-over-one plain weave patterns or two-over-two basket weave patterns, and may typically range in pitch, or pic count from 30 to 70 pics per inch. Braided reinforcement layer 220 may include a plurality of filaments having the same material and cross sectional shape, or layer 220 may have a combination of filaments that differ from one another in at least one aspect. In the current embodiment of aspiration catheter 300, reinforcement layer 220 comprises a hybrid basket weave of two differently-dimensioned flat wires, both wires being made of 304V stainless steel. Reinforcement layer 220 may include interstices formed within a mesh or formed between filaments that are applied around liner 215.

Jacket 230 provides support to catheter shafts 204, 304 and coverage of reinforcement layer 220. Jacket 230 is coaxial with liner 215 and reinforcement layer 220, and may be a single or unitary tube that continuously extends from proximal end 208 to distal end 206 of catheter shafts 204, 304. In an embodiment of the present disclosure, jacket 230 is manufactured of a polyamide, such as a polyether block amide copolymer or nylon 6,6. Jacket 230 may be thermoplastically extruded over, and forced into any interstices in reinforcement layer 220 to promote adhesion between the jacket material and liner 215 and to encapsulate reinforcement layer 220. In an alternative embodiment (not shown), assembly of jacket 230 over liner 215 and reinforcement layer 220 may result in liner 215 being forced into any interstices in reinforcement layer 220 to promote adhesion between the jacket material and liner 215 and to encapsulate reinforcement layer 220.

Figure 6:
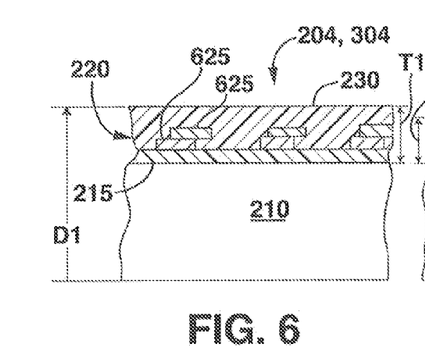
FIGS. 6 and 7 are partial longitudinal section views of the catheters of FIGS. 2-4 taken along lines 6,7-6,7 in FIG. 4.
Figure 7:
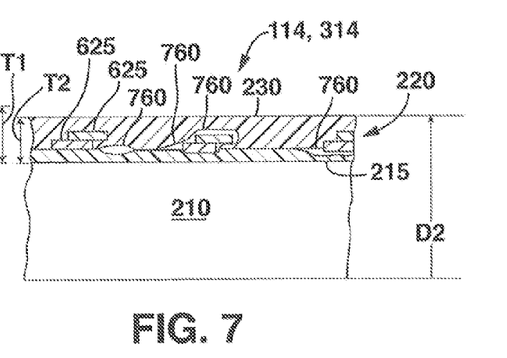

FIG. 6 shows a longitudinal semi-cross-sectional view of an embodiment of the composite laminated wall structure of catheter shafts 204, 304. Jacket 230 is shown extending through interstices between braid filaments 625 to adhere to liner 215 and encapsulate reinforcement layer 220, FIG. 7 illustrates, also in longitudinal semi-cross-section, mechanically deformed segments 114, 314 that have increased flexibility, viz. reduced bending stiffness, as compared to undeformed segments of catheter shafts 204, 304, shown in FIG. 6. Segments 114, 314 may be deformed using a radial or diametric compression process such as rolling, swaging, rotary swaging, roller swaging, hydraulic swaging, and radial forging, which processes will be described in further detail below. Besides the radial or diametric compression stresses applied by the processes discussed herein, it will be understood that any other type of mechanical stress, such as tension, torsion or bending can be applied to catheter shafts 204, 304 to result in reduced bending stiffness. The selected mechanical deformation process subjects the wall in shaft segments 114, 314 to one-time or repeated cyclic stresses sufficient to create one or more physical changes in the composite laminated wall structure; the physical changes reducing the bending stiffness of the catheter shaft. The action or resulting effects of mechanical deformation of the catheter material may be described as work softening, a demonstrable phenomenon known in fields of metallurgy and geology as being opposite to work hardening.

One of the physical changes that may result from the mechanical deformation of catheter shaft segments 114, 314 is the formation or enlargement of one or more regions 760 of delamination in the composite laminated wall structure. Prior to mechanical deformation of segments 114, 314, delamination regions 760 may be securely laminated within shafts 204, 304, as discussed above. However, given the complexity and/or uneven texture of the surfaces to be laminated, and the possible presence of contaminates such as wire-drawing lubricants that may be left on braiding filaments 625, some delamination regions 760 may already be present within shafts 204, 304 prior to mechanical deformation of segments 114, 314. As shown in FIG. 7, delamination regions 760 may occur or be enlarged between jacket 230 and liner 215, e.g. in the interstices of reinforcement layer 220. One or more delamination regions 760 may also be created or enlarged adjacent filaments 625 to at least partially loosen the previously formed encapsulation of reinforcement layer 220 by the surrounding materials of jacket 230 and/or liner 215.

Thus, the deformation process may be considered as intentionally imparting a controlled or limited degree of damage to selected segments 114, 314 of the laminated structure of catheter shafts 204, 304. Delamination regions 760, singly or in combination act as loose cells, to reduce the bending stiffness of shafts 204, 304 by allowing the adjacent shaft elements to slide or move relative to each other during bending of shaft segments 114, 314. A plurality of delamination regions 760 may be distributed somewhat randomly within the wall of shaft segments 114, 314, or regions 760 may be distributed in a substantially uniform pattern to provide a substantially consistent reduction in stiffness along segments 114, 314.

Another physical change that may result from the mechanical deformation of catheter shaft segments 114, 314 is burnishing the surfaces of braid filaments 625 where they contact each other, thus reducing inter-filament friction and the associated contribution to total bending stiffness of catheter shaft segments 114, 314. The one-time or repeated cyclic rubbing of one filament against another during mechanical deformation of catheter shaft segments 114, 314 may burnish the contacting filament surfaces. If filaments 625 make point contact with each other, as occurs when one round wire crosses another round wire, or when two flat wires are not parallel and cross each other edge-to-edge, then the mechanical deformation of catheter shaft segments 114, 314 may change the contact points on each side of a filament intersection into burnished engaged notches. Such burnished engaged notches may have reduced friction against each other as a result of a reduced coefficient of friction and/or reduced normal forces due to displacements of material from the points of contact.

Another physical change that may result from the mechanical deformation of catheter shaft segments 114, 314 is the permanent reduction in wall thickness T1 of shafts 204, 304 to wall thickness T2 of segments 114, 314, as shown in FIGS. 6 and 7. Because the catheter shaft materials are generally not compactable, mechanical deformation may thin the catheter walls by displacing material(s) longitudinally. Such an increase in length of deformed segments 114, 314 can be planned-for in the design of catheters 100, 300, or any excess length can be trimmed as desired. Because the materials of filaments 625 are usually particularly incompressible, reduced wall thickness T2 may typically be accomplished by thinning jacket 230 and/or liner 215.

In an embodiment of the disclosure, another physical change that may result from the mechanical deformation of catheter shaft segments 114, 314 is a permanent reduction in the pitch of reinforcement layer 220. In braided or spirally wound reinforcement layers, measurement units of pitch typically reflect the number of filament turns or "pics" per unit length, e.g. pics per inch. In embodiments where mechanical deformation permanently thin the catheter walls by displacing materials longitudinally, reinforcement filaments 625 are axially separated to longitudinally expand the interstices, thus reducing the pitch in reinforcement layer 220. Changing the pitch of braided catheter shafts is known by those skilled in the art to affect the stiffness of a catheter shaft. Although reducing braid pitch typically increases the bending stiffness of a reinforced catheter shaft, in accordance with the disclosure, this affect is more than counterbalanced by other physical changes that may occur in deformed segments 114, 314 to achieve an overall reduction in segment stiffness.

Yet another physical change that may result from the mechanical deformation of catheter shaft segments 114, 314 is the permanent reduction in diameter D1 of shafts 204, 304 to diameter D2 of segments 114, 314, as shown in FIGS. 6 and 7. FIGS. 2 and 3 also illustrate, with exaggeration for clarity, segments 114, 314 being stepped down in diameter relative to shafts 204, 304. However, it should be understood that segments 114, 314 may have little or no permanent change in any physical dimensions following deformation; segments 114, 314 relying instead on other physical changes therein to provide the desired reduction in stiffness. In embodiments where it is desirable to maintain the diameter of bore 210 substantially uniform throughout the catheter, reduced diameter D2 is achieved substantially by permanently reducing wall thickness from T1 to T2, as described above. The diameter of bore 210 can be maintained during the deformation process by supporting bore 210 with an incompressible mandrel, as will be described below.

Table 1 shows a measured reduction in stiffness resulting from mechanical deformation on one set of sample shaft segments. The samples were mechanically deformed in a rotary swager using a die set having a diameter of 1.23 mm (0.049 in). In these samples, bore 210 was uniformly maintained with a mandrel having a diameter of 1.04 mm (0.041 in). The pre-deformation outside diameter of 1.37 mm (0.054 in) was permanently reduced to an outside diameter of 1.32 mm (0.052 in), which is larger than the die set diameter of 1.23 mm (0.049 in). This result indicates an amount of "spring back," in the sample shaft segments from the size of the die set, viz., the rotary swaging resulted in a combination of elastic and plastic deformation in diameter of the samples. The average bending stiffness was reduced by 28% with a permanent diameter reduction of 4%. The braid pitch was permanently reduced by 10%, which would typically increase the stiffness of a reinforced catheter shaft, as described above. Thus, the potentially undesirable increase change in braid stiffness was more than offset by one or more other physical changes brought about by mechanical deformation of the samples.

TABLE 1

|  | Outside Diameter | Braid Pics/inch | Stiffness |
|---|---|---|---|
| Not Deformed | 1.37 mm (0.054 in) | 86.5 | 63.5 |
| Deformed | 1.32 mm (0.052 in) | 77.5 | 45.5 |

Figure 13:
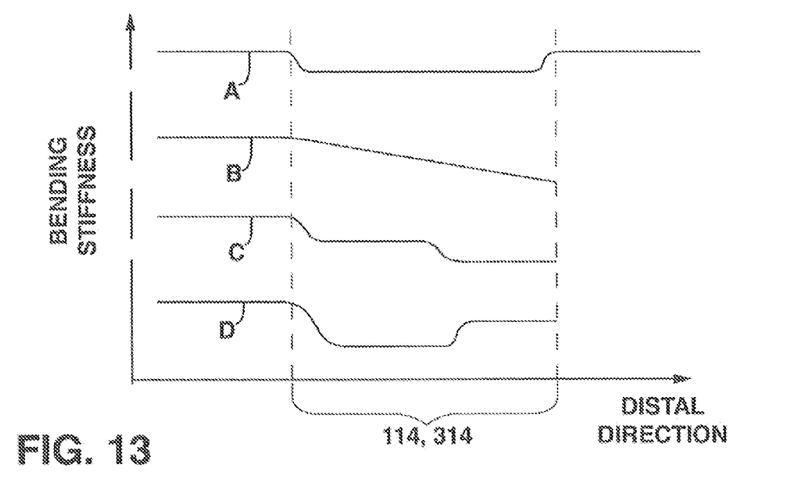
FIG. 13 is a prophetic graphic illustration of the bending stiffness profile of several catheters as may be made according to the invention.

FIG. 13 is a prophetic graphical illustration of the bending stiffness of prophetic catheters A-D, as measured along a portion of the catheter shafts including segments 114, 314. The stiffness profiles of prophetic catheters A-D are arranged on a single graph to make efficient use of drawing space, and are not necessarily positioned for quantitative comparison to each other along the vertical axis of FIG. 13.

In another embodiment of the disclosure, the degree or amount of mechanical deformation of catheter shaft segments 114, 314 may be selectively varied to achieve a reduction in bending stiffness that varies along the length of segments 114, 314. Prophetic catheter A is illustrated as having a constant bending stiffness along segments 114, 314, the bending stiffness of segments 114, 314 being less than the bending stiffness of adjacent portions of the catheter shaft that have not been mechanically deformed. The constant bending stiffness illustrated along segments 114, 314 is associated with uniform distribution of any of the physical change(s) discussed above, and results from consistent mechanical deformation along segments 114, 314.

Prophetic catheter B is illustrated as having a bending stiffness that decreases continuously in a distal direction along catheter shaft segments 114, 314. As shown for catheters B-D, no stiffness is measured distally of catheter segments 114, 314, indicating that no portion of catheter shafts 204, 304 extends beyond catheter segments 114, 314. In alternative embodiments (not shown), bending stiffness could decreases continuously in a proximal direction along catheter shaft segments 114, 314, and/or a distal portion of catheter shafts 204, 304 could extend beyond catheter segments 114, 314. The graphical stiffness profile of catheter B may be achieved by continuously changing the amount of mechanical deformation applied to catheter segments 114, 314 as they are passed through a deforming apparatus, as will be discussed in further detail below. A relatively less-stiff portion of segments 114, 314 indicates that such a portion received a greater amount of mechanical deformation than a relatively stiffer portion of segments 114, 314.

Prophetic catheter C is illustrated as having a bending stiffness that decreases discontinuously, in multiple steps in a distal direction along catheter shaft segments 114, 314. The graphical stiffness profile of catheter C may be achieved by applying mechanical deformation in two steps to catheter segments 114, 314 as they are passed through a deforming apparatus.

Prophetic catheter D is illustrated as having, like sample catheter C, a bending stiffness that decreases discontinuously, in multiple steps in a distal direction along catheter shaft segments 114, 314. However, in catheter D, although both steps in the stiffness profile represent measured stiffnesses that are less than portions of the catheter that have not been mechanically deformed, the stiffness of more distal portion or step is actually greater than the stiffness of more proximal portion or step.

Figure 14:
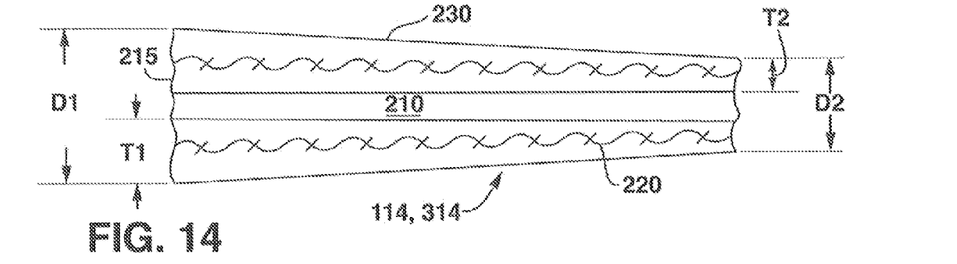
FIGS. 14 and 15 are longitudinal cross-sections of mechanically deformed catheter shaft segments according to an embodiment of the present disclosure.
Figure 15:
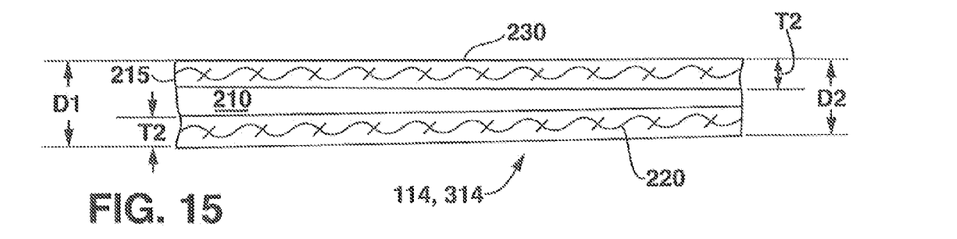

FIGS. 14 and 15 are longitudinal cross-sections of catheter shaft segments 114, 314 that illustrate continuous dimensional change resulting from continuous variation in the amount of mechanical deformation applied along portions of segments 114, 314, as may occur in catheter sample A, discussed above. FIG. 14 illustrates segments 114, 314 wherein bore 210 has a constant diameter. The catheter wall thickness tapers continuously along segments 114, 314 from thickness T1 to reduced wall thickness T2, and the catheter diameter tapers continuously from diameter D1 to reduced diameter D2. Also refer to FIGS. 6 and 7.

FIG. 15 illustrates segments 114, 314 wherein bore 210 has a distally tapered diameter. Catheter wall thickness T2 remains constant along segments 114, 314, and the catheter outside diameter tapers continuously from diameter D1 to reduced diameter D2. Also refer to FIGS. 6 and 7.

Figure 8:
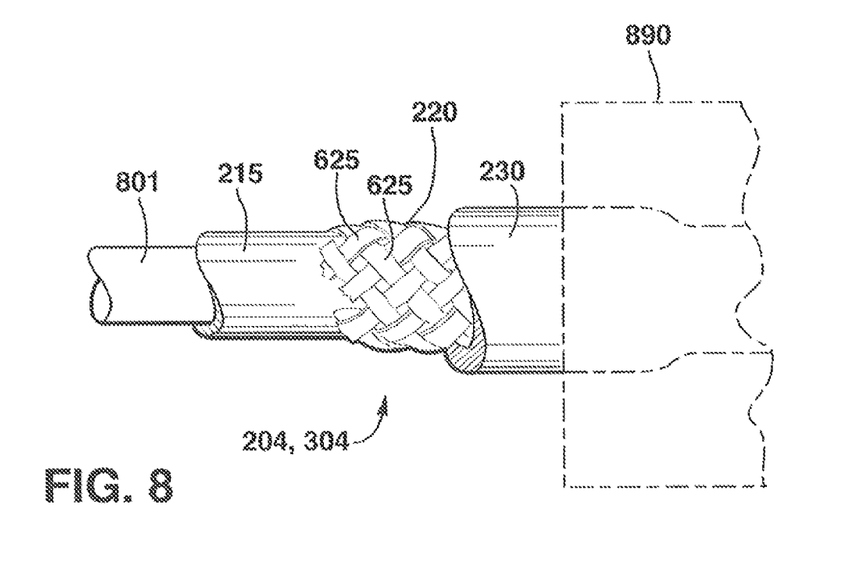
FIG. 8 illustrates a cutaway view of a catheter according to an embodiment of the present disclosure, shown inserted into a schematic, depiction of a deforming apparatus.
Figure 9:
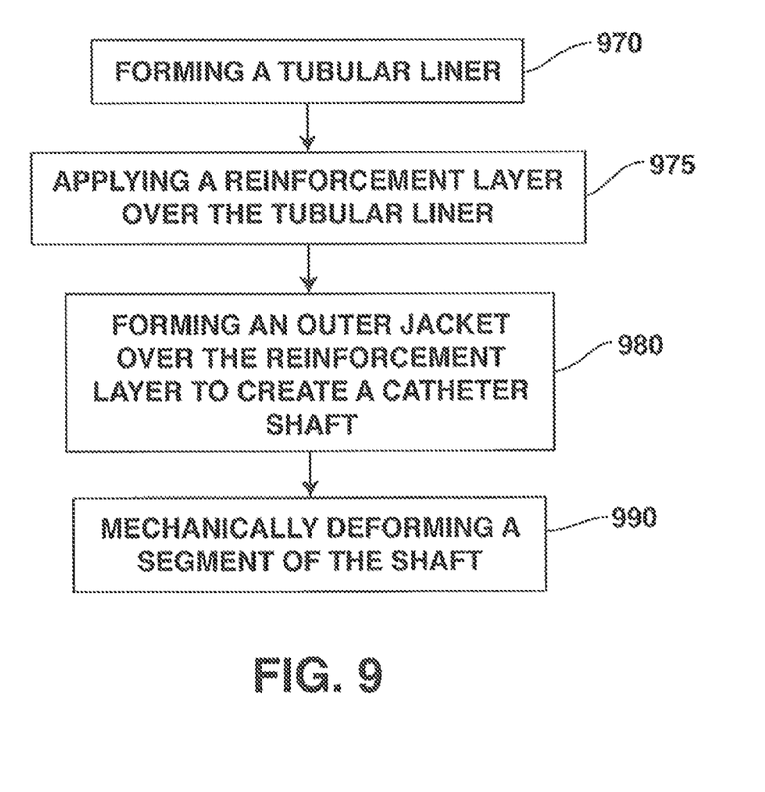
FIG. 9 schematically illustrates a process for making a catheter according to an embodiment of the present disclosure.

An embodiment of the present disclosure includes a method of manufacturing catheter shafts 204, 304 having segments that are selectively made more flexible by a mechanical deformation or work softening process. In one embodiment, as shown in FIG. 8, and schematically illustrated in step 970 of the flow chart depicted in FIG. 9, elongate reinforced composite tubing to be used for catheter shafts 204, 304 is formed in a first step of extruding a thermoplastic material, such as 70D PEBA, optionally over a mandrel 801, to form tubular liner 215. Mandrel 801 may comprise an elongate wire or plastic core, and defines the final diameter of bore 210. Using a melt-extrusion process in step 970, many lengths of liner 215 may be continuously formed, and wound on a reel for storage, if desired. In step 975, flat stainless steel wires 625 are selected and braided over liner 215 to form reinforcements layer 220, passing the long subassembly from reel to reel. In step 980, a jacket material, such as a polyamide, is thermoplastically extruded over reinforcement layer 220 to form jacket 230, again passing the long subassembly from reel to reel. Jacket 230 may extend through the interstices of braided reinforcement layer 220 to form a bond with liner 215, as shown in FIGS. 6 and 7. Alternatively, an adhesive or other type of tie layer material may be incorporated to bond together liner 215, reinforcement layer 220, and jacket 230, as would be well known to those of skill in the art.

The elongate composite laminated tubing subassembly is then drawn from a reel and is cut in appropriate lengths to form a number of catheter shafts 204, 304. Shaft 204 may, e.g. be approximately 100 cm long for use in guiding catheter 100. Shaft 304 may, e.g. be approximately 140 cm long for use in aspiration catheter 300. In accordance with alternative methods, catheter shafts 204, 304 may be fabricated one at a time instead of using continuous or reel-to-reel processes. Such one-at-a-time catheter manufacturing is less efficient than reel-to-reel processing, but this process may be useful if one or more selected plastic materials, e.g., PTFE, require paste extrusion, which cannot produce very long extrudates. If mandrel 801 was used during manufacturing, then it is removed from catheter hafts 204, 304 to provide open bore 210.

Figure 10:
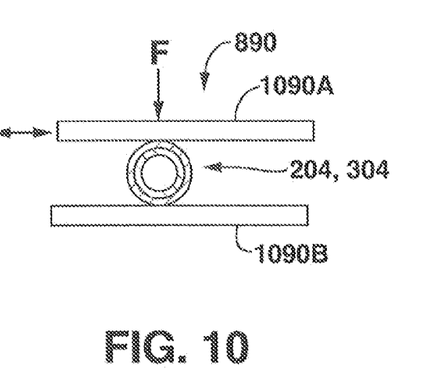
FIG. 10 illustrates an apparatus for rolling a catheter according to an embodiment of the present disclosure.

In step 990, segments 114, 314 of catheter shafts 204, 304 are mechanically deformed in a deforming apparatus 890. FIG. 10 illustrates a first example, in which deforming apparatus 890 comprises a pair of platens 1090A, 1090B for rolling shafts 204, 304 laterally there between under diametrical pressure F to mechanically deform segments 114, 314. Platens 1090A, 1090B may be reciprocated relative to each other until the desired physical changes have been effected in segments 114, 314. Alternatively, deforming apparatus 890 may comprise a pair of opposed, non-reciprocating jaws similar to platens 1090A, 1090B, the jaws being usable for hydraulically swaging or forging shafts 204, 304 laterally there between under diametrical pressure to mechanically deform segments 114, 314.

Figure 11:
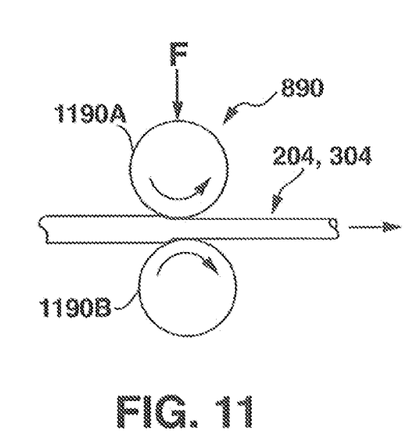
FIG. 11 illustrates an apparatus for roller swaging a catheter according to an embodiment of the present disclosure.

FIG. 11 illustrates an example of a roller swaging process, wherein deforming apparatus 890 comprises a pair of pinch rollers 1190A, 1190B for rolling shafts 204, 304 axially there between under diametrical pressure F to mechanically deform segments 114, 314. Rollers 1190A, 1190B may be circumferentially grooved (not shown), and/or used in skewed sequential pairs for distributing mechanical deformation forces more uniformly about the circumferences of shafts 204, 304.

Figure 16:
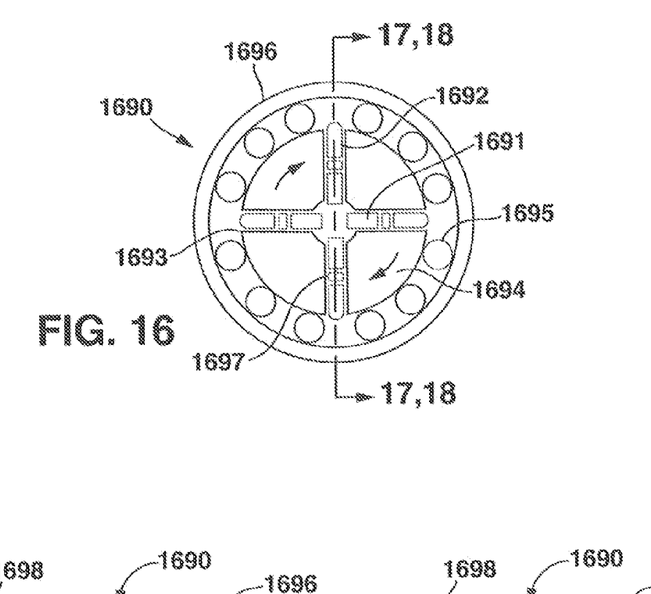
FIG. 16 illustrates a front view showing the main parts of a roller swager according to an embodiment of the present disclosure.
Figure 17:
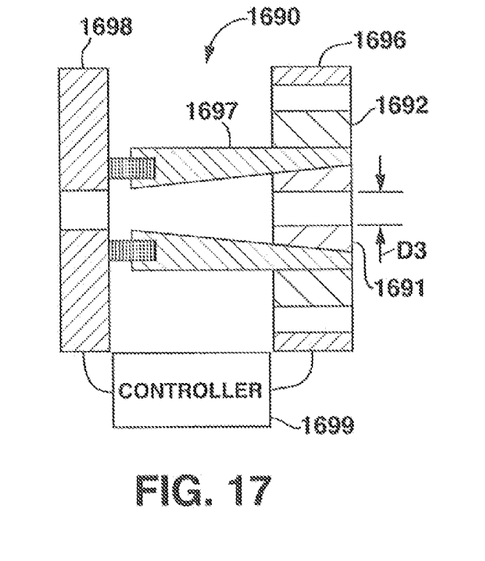
FIGS. 17 and 18 illustrate cross-sectional side views of the roller swager of FIG. 16, taken along lines 17-17 and 18-18 respectively.
Figure 18:
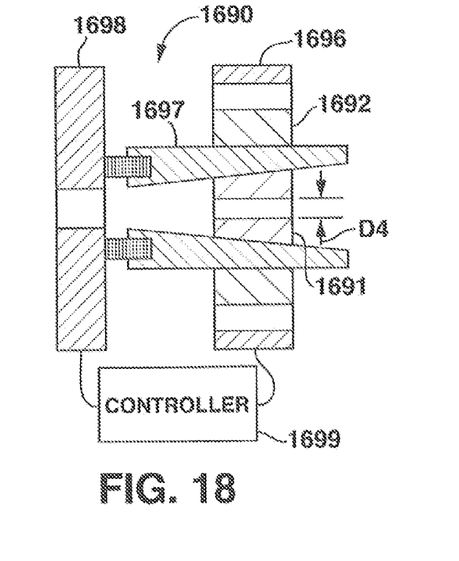

A deforming apparatus for use in the disclosure may also comprise alternative swaging mechanisms such as a rotary swager 1690, the main parts of which are shown assembled in FIGS. 16-18. Similar to classical rotary swagers well-known to those of skill in the art, rotary swager 1690 comprises a plurality of dies 1691 and hammers or backers 1692 slidably disposed within radial slots 1693 in a rotatable spindle 1694. Rotary swager 1690 is shown in FIG. 16 as having four dies, but two or three dies are alternative configurations. Spindle 1694 rotates within a series of rollers 1695 arranged circumferentially within non-rotating head 1696. Rollers 1695 drive backers 1692 against dies 1691 toward the center of spindle 1694. Tangential inertia, the fictitious "centrifugal force," tends to keep dies 1691 away from the center of rotation when they are momentarily disposed between rollers 1695. Dies 1691 cyclically close over shafts 204, 304 to deform the material into segments 114, 314. Shafts 204, 304 can be plunged, viz. inserted and withdrawn from the center of dies 1691 of rotary swager 1690.

Rotary swager 1690 may also be provided with an engagement/disengagement feature whereby the interaction of dies 1691, backers 1692 and rollers 1695 can be selectively operated while, spindle 1694 rotates within head 1696. Such a feature may allow shafts 204, 304 to be axially moved in rotary swager 1690, without deformation, to and from a location where swaging is desired. In this way, swaging may be performed at selected locations of shafts 204, 304 besides at the ends.

In an embodiment of the disclosure, the engagement/disengagement feature of rotary swager 1690 may also be finely controlled such that the degree or amount of mechanical deformation achieved by swaging is selectively increased or decreased while catheter shaft segments 114, 314 are passed through dies 1691. The resulting reduction in bending stiffness along segments 114, 314 may be continuous, discontinuous, increasing or decreasing, as discussed above. The reduction in stiffness may, if desired, change very gradually along the segments 114, 314. Thus, segments 114, 314 may, if desired, extend the full length of catheters 204, 304 to provide catheters with reduced and varied bending stiffness along the entire length of the catheters.

FIGS. 16-18 illustrate one embodiment for providing fine control of the amount of mechanical deformation by rotary swager 1690. Wedges 1697 are slidably mounted between, and rotate with backers 1692 and dies 1691. Wedges 1697 extending generally parallel to the rotational axis of swager 1690. The closed diameter or transverse dimension of dies 1691 is adjusted by the variable depth to which wedges 1697 are inserted between backers 1692 and dies 1691. FIG. 17 shows each wedge 1697 positioned such that the narrowest wedge dimension is inserted between backers 1692 and dies 1691 providing a relatively large closed transverse dimension 93 between opposing dies 1691. FIG. 18 shows each wedge 1697 positioned such that a wider wedge dimension is inserted between backers 1692 and dies 1691, providing a relatively smaller closed transverse dimension D4 between opposing dies 1691.

A set of rotary swaging dies is conventionally designed such that the dies abut each other when closed to form a cavity having a desired diameter and/or shape to be imparted to the swaged article. However, rotary swager 1690 is intended to provide a variable amount of mechanical deformation along the length of an article such as a catheter without changing die sets. Therefore, the forming surfaces of dies 1691 need not be shaped to form a cavity. Rather, the forming surfaces of dies 1691 may be flat, or have a concave surface with a radius of curvature suitable for forming diameters equal to or greater than the largest desired diameter, e.g., transverse dimension D3.

An exposed end of each wedge 1697 revolves in contact with swash plate 1698, which is rotationally fixed, but axially movable with respect to head 1696. The exposed ends of wedges 1697 may have anti-friction blocks or rollers riding on the surface of swash plate 1698. Swash plate 1698 may have a central opening such that elongate work pieces may be passed axially through rotary swager 1690, viz., through dies 1691 and swash plate 1698 during the swaging process. Swash plate 1698 is held parallel to head 1696) such that the insertion depths of wedges 1697 are maintained constant for a given distance between swash plate 1698 and head 1696. Moving swash plate 1698 along the rotational axis of swager 1690 toward head 1696 drives wedges 1697 farther between backers 1692 and dies 1691. When swash plate 1698 is moved away from head 1696, wedges 1697 are squeezed or forced from between backers 1692 and dies 1691 to maintain contact between wedges 1697 and swash plate 1698.

Controller 1699, illustrated schematically in FIGS. 17 and 18, controls the axial distance between awash plate 1698 and head 1696, and thus controls the insertion depth of wedges 1697 between backers 1692 and dies 1691. Controller 1699 may be a device that is mechanical, electro-mechanical, hydro-mechanical or other type of positioning mechanism, e.g., a linear actuator, a lead screw or a ball screw.

In an alternative embodiment of rotary swager 1690, swash plate 1698 may be replaced with a rotating actuator plate (not shown), to which the ends of wedges 1697 are attached such that axial movement of the actuator plate can not only push wedges 1697 in between backers 1692 and dies 1691, but can also withdraw wedges 1697. In this embodiment, controller 1699 may require a thrust bearing to control the position of the rotating actuator plate. Besides roller swager 1690, other types of deforming apparatus 890, as discussed above, may be finely controlled such that the degree or amount of mechanical deformation achieved is selectively increased or decreased while catheter shaft segments 114, 314 are passed through deforming apparatus 890.

Mandrel 801 may be left in place during a mechanical deformation step to support bore 210. Alternatively, mandrel 801 may be removed and replaced with a different, e.g., harder mandrel. For example, elongate mandrel 801 may comprise an extrudable thermoplastic, e.g., acetal resin, for the reel-to-reel steps of manufacturing. Then, the acetal mandrel 801 may be replaced with a metal, e.g., stainless steel mandrel for the deformation step. Using a rigid support mandrel may also permit one-sided deformation of catheter shafts 204, 304, viz. applying radial, rather than diametrical compression. Next, the remaining components, e.g., a soft tip and/or fitting 102 are secured to catheters 100, 300. In guiding catheter 100 a desired curvilinear shape is heat-set into a distal portion of shaft 104.

Figure 12:
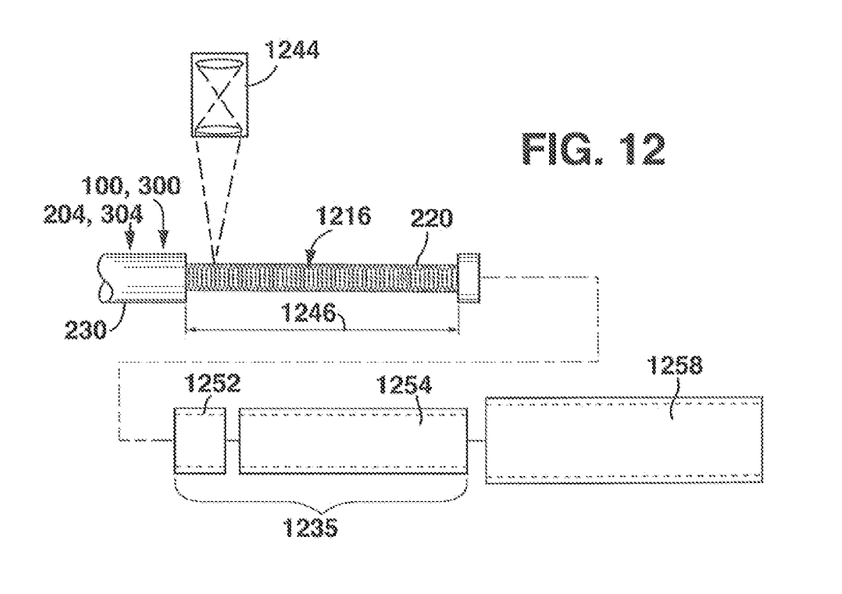
FIG. 12 illustrates a side assembly view of a portion of a catheter shaft according to an embodiment of the present disclosure showing a groove, a fill section and a sleeve.

As illustrated in FIG. 12, catheter shafts 204, 304 can optionally include an annular shaped, circumferentially extending groove 1216, which may be cut out of catheter shafts 204, 304 as described in U.S. Pat. No. 6,375,774, which is incorporated herein by reference in its entirety. Groove 1216 may provide one or more additional portions of varying stiffness in catheter shafts 204, 304 or in deformed segments 114, 314. Further, groove 1216 may provide a transition region between relatively stiffer and relatively more flexible portions of catheter shafts 204, 304 or deformed segments 114, 314. This transition region may prevent or reduce kinking and/or collapsing of catheters 100, 300 and may provide improved tracking and movement in a patient's vessel.

Fill section 1235 may comprise one or more fill components 1252, 1254 having hardness(es) different from the hardness of jacket 230; fill section 1235 being positionable in groove 1216 to provide variable flexibility to catheter shafts 204, 304 or deformed segments 114, 314. Alternatively, fill section 1235 may comprise guidewire tube 550 and over sleeve 355 to make dual lumen portion 316 of shaft 304, as discussed above regarding FIGS. 3 and 5. In an embodiment of catheter shaft 204, groove 1216 may be located adjacent the shaft distal end of and have a groove length 1246, e.g., of approximately three centimeters. In this embodiment, the groove depth may be approximately equal to the thickness of outer jacket 230. Fill components 1252, 1254 may include thermoplastic materials similar to the materials discussed above regarding jacket 230, such as amides or blends thereof, and can be manufactured, e.g., by extrusion. In an embodiment of catheter shaft 304, groove 1216 may have a groove length 1246, e.g., of approximately 9 centimeters, FIG. 12 also illustrates a tubular sleeve 1258 which can be used to attach guidewire tube 550 and over sleeve 355 to shaft 304, or to attach fill components 1252, 1254 to catheter shaft 204. Sleeve 1258 may be a piece of shrink tubing which is heated above the glass transition temperatures of over sleeve 355 or the fill components 1252, 1254, whereupon sleeve 1258 shrinks and compresses heat-softened elements such as over sleeve 355 or fill components 1252, 1254 into groove 1216, according to methods disclosed in the '774 patent.

Groove 1216 may be formed in a portion of jacket 230 with a removing device 1244, which may be, e.g., a grinding wheel, an abrasive brush, or an excimer laser. The excimer laser may remove a selected portion of jacket 230 without damaging reinforcement section 220. Further, the excimer laser may remove material in the interstices of reinforcement section 220, allowing for a stronger bond between the fill section 1235, reinforcement section 220 and liner 215. Groove 1216 may be formed and filled with fill section 1235 before or after segment 114 is mechanically deformed in catheter shaft 204

While the particular medical catheters 100, 300 as herein shown and disclosed in detail are fully capable of obtaining the objects and providing the advantages herein before stated it is to be understood that they are merely illustrative of the presently preferred embodiments of the disclosure and that no limitations are intended to the details of construction or design herein shown other than as described in the appended claims.

What is claimed is:

1. A medical catheter comprising:
   a composite elongate catheter shaft comprising:
      a flexible polymeric liner;
      a flexible polymer jacket adherently surrounding the liner;
      a reinforcement layer interposed between the liner and the jacket; and
      at least one segment of the composite shaft having internal radial compressive structural deformations characterized by a reduction in longitudinal bending stiffness of the segment such that the longitudinal bending stiffness varies along the length of the segment containing the deformations; and
   a fitting mounted at a proximal end of the shaft.

2. The medical catheter of claim 1 wherein the catheter shaft further comprises a wall, the wall, in the at least one shaft segment having deformations being thinner than the wall of a shaft segment without such structural deformations.

3. The medical catheter of claim 1 wherein the catheter shaft further comprises a substantially uniform diameter bore extending therethrough.

4. The medical catheter of claim 1 wherein in the at least one segment having deformations, the reinforcement layer comprises one or more filaments braided about the liner and forming a plurality of interstices, the jacket and the liner being adhered to each other through the interstices.

5. The medical catheter of claim 4 wherein the at least one shaft segment has a braid pitch that is less than a braid pitch of a segment of the shaft that is without such structural deformations.

6. The medical catheter of claim 1, wherein the internal radial compressive deformations comprise a plurality of regions of delamination.

7. The medical catheter of claim 6, wherein the regions of delamination are distributed within the wall of the at least one segment having the deformations to provide a substantially consistent reduction in stiffness.

8. The catheter of claim 1, wherein the stiffness of the at least one segment having the deformations decreases in a distal direction.

9. The catheter of claim 8, wherein the stiffness of the at least one segment having the deformations decreases continuously in the distal direction.

10. The catheter of claim 1, wherein the stiffness of the at least one segment containing the deformations varies discontinuously.

11. The catheter of claim 1, wherein a distal portion of the catheter has a preformed curvilinear shape.

* * * * *